United States Patent [19]

Bertelli

[11] Patent Number: 5,135,946
[45] Date of Patent: Aug. 4, 1992

[54] USE OF 2,4 MONOFURFURYLIDENE-SORBITOL AND ITS TETRAALKYL DERIVATIVES IN COSMETICS AND DERMATOLOGY

[75] Inventor: Vittorio Bertelli, Milan, Italy

[73] Assignee: Laboratori Fitocosmesi e Farmaceutici S.r.l., Italy

[21] Appl. No.: 457,189

[22] Filed: Dec. 26, 1989

Related U.S. Application Data

[63] Continuation-in-part of Ser. No. 194,896, May 17, 1988, abandoned.

[30] Foreign Application Priority Data

May 28, 1987 [IT] Italy ............................. 20707 A/87

[51] Int. Cl.$^5$ .............................................. A61K 31/34
[52] U.S. Cl. .................................................... 514/461
[58] Field of Search ......................................... 514/461

[56] References Cited

U.S. PATENT DOCUMENTS 3,383,279  5/1968  Garzia ................................... 167/55
3,551,554 12/1970  Herschler ............................... 424/7
4,557,934 12/1985  Cooper ................................. 424/128

FOREIGN PATENT DOCUMENTS 1091134 11/1967 United Kingdom .

OTHER PUBLICATIONS

Lackman et al., "The Theory & Practice of Industrial Pharmacy" 2 Ed., 1976, pp. 235, 238–240.
Chemical Abstract, vol. 97, 1982, No. 174654.

Primary Examiner—Leonard Schenkman
Attorney, Agent, or Firm—Parkhurst, Wendel & Rossi

[57] ABSTRACT

The use of 2,4-monofurfurylidene-sorbitol and 2,4-monofurfurylidene-1,3,5,6-0-tetraalkylsorbitol wherein the alkyls are linear or branched $C_1$–$C_4$, in the preparation of cosmetics and dermatology compositions for preventing premature ageing of the skin caused by free radicals which form in the skin either physiologically or by the effect of environmental pollutant substances or radiation.

Said compositions are in the form of creams, gels, lotions, sprays, etc., and contain between 0.5 and 2% by weight or 2,4-monofurfurylidene-sorbitol or 2,4-monofurfurylidene-1,3,5,6-0-tetraalkylsorbitol.

5 Claims, No Drawings

USE OF 2,4 MONOFURFURYLIDENE-SORBITOL AND ITS TETRAALKYL DERIVATIVES IN COSMETICS AND DERMATOLOGY

This application is a continuation-in-part of Ser. No. 07/194,896, filed May 17, 1988, now abandoned.

This invention relates to the use of 2,4-monofurfurylidene-sorbitol and its tetraalkyl derivatives in the preparation of cosmetics and dermatology compositions.

More particularly, the invention relates to the use of 2,4-monofurfurylidene-sorbitol and 2,4-monofurfurylidene-1,3,5,6-O-tetra-alkyl-sorbitol wherein the alkyls are linear or branched $C_1$-$C_4$, in the preparation of cosmetics and dermatology compositions for preventing premature aging of the skin.

Skin aging, resulting in the loss of elasticity, the formation of dark spots and the appearence of lines, is caused mainly by the free radicals which form either physiologically by metabolic processes in the skin cells, or by the action of solar ionizing or atomic radiation or of pollutant substances in the atmosphere or environment.

Atmospheric pollutants include in particular the fumes from industrial chimneys and the exhaust gas of internal combustion engines;

environmental pollutants include in particular tobacco smoke; and ultraviolet rays constitute the main harmful factor of solar radiation.

Said pollutant substances and said radiation increase the formation of free radicals to thus accelerate the skin aging process, and in addition can cause serious harm such as skin tumours.

It is well known that free radicals are very reactive unstable chemical structures which give rise to chain reactions (L. B. Myers, Fed. Proc: 32, 1882 (1973)). If the random agents are polycyclic hydrocarbons contained in the industrial fumes or engine exhaust gas, or X-rays, gamma-rays, UV-rays or higher-frequency visible radiation, the reaction chain commences during exposure by the effect of the supplied energy which is transferred to an electron by the Compton or photoelectric effect. The electron travels within the medium with the formation of ionized molecules which produce highly reactive radicals.

These radicals exert a basic influence on the skin aging processes by reaction with the proteins, lipids and nucleic acids of the cutaneous cells.

2,4-monofurfurylidene-sorbitol is known to be a substance suitable for pharmaceutical use, such as in the treatment of hepatic and intestinal disturbances (U.S. Pat. No. 3,383,279).

We have now found that the application of 2,4-monofurfurylidene-sorbitol and its tetraalkyl derivatives of the present invention prevent the formation of free radicals either of endogenous or exogenous origin, and also arrest their action if they existed before the application.

The action mechanism of said compounds is different from that of vitamins E, A, K and C in that these possess only antioxidant action, and not antiradical action.

The existence of free radicals is shown by ERS signals, and these are easily detected in the skin after exposure of the aforesaid agents.

Thus, the object of the present invention is to provide cosmetic and dermatologic compositions for topical cutaneous application useful for preventing or eliminating the effects of free radicals.

After several applications on persons of both sexes having derma in normal or in pathologic status (erythema, itching derma and so on), no phenomena occurred showing intolerance to the product. Experimental tests proved that the 2,4-monofurfurylidenesorbitol protects the rats from the acute intoxication due to $CCl_4$ or allyl alcohol. The hepatic damage due to these substances occurs through the formation of free radicals and consequently the reduction of the free radicals in the presence of the 2,4-furfurylidene-sorbitol is proved.

In another test fibroblasts cells derived from human embryonic skin and lung were damaged by exposing the cells to the action of tert.butyl-hydroperoxide, and lactate dehydrogenase (LDH) released from damaged cells, was determined after 4, 5 and 6 hours. The specimens previously treated with 2,4-furfurylidene-sorbitol showed LDH release respectively 55%, 73% and 74% of the non treated specimens. Thus the free radical scavenging and antioxidant properties of the product are confirmed.

The compositions of the invention are prepared for cutaneous application in various product forms such as creams, gels, lotions, sprays etc. Topical application of these compositions prevents derma damages caused by radiation and by the atmospheric agents which produce the free radicals in the skin which cause premature aging.

Said compositions have a content of the 2,4-monofurylidene-sorbitol or its tetraalkyl derivatives of between 0.5 and 2% by weight and preferably between 0.7 and 1.5% by weight and comprise the usual components known to the cosmetics art such as vaseline oil, glycols, triethanolamine, perfume etc.

The composition is prepared under hot conditions while stirring. The preparation temperature is between 60° and 85° C. and preferably between 70° and 75° C., the composition then being left to cool to ambient temperature while stirring.

The following examples of cosmetics and dermatology compositions according to the present invention, for the prevention of skin aging, are given hereinafter by way of non-limiting illustration.

EXAMPLE 1

| Preparation of an O/W cream | % by weight |
| --- | --- |
| A) Beeswax/PEG 8 (APIFIL-GATEFOSSE) | 8 |
| Vaseline oil | 15 |
| Polypropylene glycol | 7 |
| B) Demineralized water | 67.8 |
| 2,4-monofurfurylidene-sorbitol | 1 |
| Methylchloroisothiazolinone and Methylsothiazolinone (ROHM AND HAAS C.) | 0.1 |
| Carbomer 934 (T.M. GOODRICH) | 0.3 |
| Sodium dehydroacetate | 0.2 |
| C) Triethanolamine (50% solution) | 0.6 |
| Perfume | as required |
| Total | 100 |

A) The mixture of beewax, vaseline oil and propylene glycol is melted.

B) The water is heated to 70° C.; the 2,4-monofurfurylidene-sorbitol and the other components are added and the mixture left to stand.

A) and B) are heated separately to 75° C. after which B) is poured into A) while stirring.

C) The TEA solution is added, the mixture cooled to 35° C. while stirring and perfume added.

EXAMPLE 2

| Preparation of a W/O cream | % by weight |
| --- | --- |
| A) Copolymer (22) ethylene oxide and dodecylglycol (Elfacos ST37 = AKZO CHEMIE) | 3 |
| BHT (butylhydroxytoluene) | 0.02 |
| Hydroxyoctacosanyl hydroxystearate | 5 |
| Vaseline oil | 10 |
| Isoacetylstearate | 10 |
| Copolymer of methoxy (22) ethylene oxide and dodecylglycol (Elfacos E200 AKZO CHEMIE) | 3 |
| B) Demineralized water | 62.88 |
| 2,4-monofurfurylidene-sorbitol | 0.8 |
| Sodium dehydroacetate | 0.2 |
| Sorbitol 7 | 5 |
| C) Perfume | as required |
| Total | 100 |

A) The compound mixture is melted while stirring.
B) The water is heated to 70° C., the 2,4-monofurfurylidene-sorbitol is dissolved and the other components then added.

The mixture A) and B) are heated separately to 75° C. and B) is then poured into A) while stirring. The mixture is cooled to 35° C. while stirring and the perfume C) added.

EXAMPLE 3

| Preparation of a gel | % by weight |
| --- | --- |
| Demineralized water | 87.5 |
| 2,4-monofurfurylidene-sorbitol | 1 |
| Carbomer 940 (T.M. GOODRICH) | 0.5 |
| Sorbitol 70 | 5 |
| Glycerin | 5 |
| 50% triethanolamine solution | 1 |
| Sodium dehydroacetate | 0.2 |
| Perfume | as required |
| Total | 100 |

The 2,4-monofurfurylidene-sorbitol is dissolved in the water heated to 70° C., the carbomer is dispersed, the dispersion allowed to stand, and the following added in the stated order while stirring: sorbitol, glycerin, the TEA solution, the sodium dehydroacetate and the perfume.

EXAMPLE 4

| Preparation of a W/S cream | % by weight |
| --- | --- |
| A) Abil WE-09 (TEGO-GOLDSCHMIT) | 5 |
| Caprilic-caprinic triglyceride (Mygliol 812-DYNAMIT NOBEL) | 11 |
| PCL liquid (DRAGOCO A.G.) | 6 |
| Perfume | as required |
| B) Demineralized water | 72.5 |
| Sodium cloride | 2 |
| 2,4-monofurfurylidene-1,2,5,6-O-tetramethylsorbitol | 0.75 |
| Glycerin | 3 |
| Total | 100 |

A) The components Abil, Mygliol, PCL and the perfume are mixed.
B) Sodium chloride, 2,4-monofurfurylidene-1,3,5,6-O-tetramethylsorbitol are dissolved in the demineralized water.

The mixture B) is poured into the mixture A) while strongly stirring.

Stirring is continued for 15 minutes.

EXAMPLE 5

| Preparation of a W/S milk | % by weight |
| --- | --- |
| A) Abil WS-08 (TEGO-GOLDSCHMIT) | 5 |
| Vaseline oil | 17 |
| Mygliol 812 (DYNAMIT NOBEL) | 10 |
| Perfume | as required |
| B) Demineralized water | 58.8 |
| Sodium chloride | 2 |
| 2,4-monofurfurylidene-1,3,5,6-O-tetrapropylsorbitol | 1.2 |
| Glycerin | 3 |
| Sorbitol | 3 |
| Total | 100 |

A) The components Abil, vaseline oil, Mygliol and the perfume are mixed.
B) Sodium chloride, 2,4-monofurfurylidene-1,3,5,6-O-tetrapropylsorbitol, glycerin and sorbitol are added to the demineralized water.

The mixture B) is poured into the mixture A) while strongly stirring.

Stirring is continued for 15 minutes.

EXAMPLE 6

| Preparation of a W/O cream | % by weight |
| --- | --- |
| A) Glyceryl monostearate (ESPERIS) | 10 |
| Vaseline | 10 |
| Vaseline oil | 10 |
| Beeswax | 5 |
| Lanolin | 25 |
| Preservatives | 0.15 |
| B) Demineralized water | 39 |
| 2,4-monofurfurylidene-1,3,5,6-O-tetrabutylsorbitol | 0.85 |
| C) Perfume | as required |
| Total | 100 |

A) The mixture of glyceryl monostearate, vaseline, vaseline oil, beeswax, lanolin and preservatives is melted at 75° C.
B) The 2,4-monofurfurylidene-1,3,5,6-O- is added to the demineralized water heated to 72° C.

The mixture B) is poured into the mixture A) while stirring. When the temperature decreases to 35° C. perfume is added.

EXAMPLE 7

| Preparation of a O/W cream | % by weight |
| --- | --- |
| A) Beeswax | 5 |
| Arlacel 60 (ATLAS) | 3 |
| Tween 60 (ATLAS) | 4 |
| Hydrogenated vegetable oil (PROCTER & GAMBLE) | 17.5 |
| Vaseline light oil | 26 |
| Preservatives and antioxidants | 0.2 |
| B) Demineralized water | 38.5 |
| 2,4-monofurfurylidene-1,3,5,6-O-tetra-n-butylsorbitol | 1 |
| Sorbitol | 5 |
| Citric acid | 0.1 |
| Preservatives | 0.15 |
| Total | 100 |

A) The mixture of beeswax, Arlacel, Tween, vegetable oil, vaselin oil, preservatives and antioxidants is melted.

B) The 2,4-monofurfurylidene-1,3,5,6-O-tetra-n-butyl-sorbitol, citric acid, preservatives and antioxidants are dissolved in the demineralized water heated to 70° C.

The mixtures A) and B) are heated separately to 75° C. and B) is then poured into A) while stirring.

The mixture is cooled to 35° C. while stirring and a perfume is added.

EXAMPLE 8

| Preparation of an antisolar hydroalcoholic lotion | % by weight |
|---|---|
| A) Glyceryl-p-aminobenzoate (ESCALOL VAN DYK) | 3 |
| Propyleneglycol ricinoleate | 10 |
| Glycerin | 10 |
| Ethyl alcohol | 64 |
| Perfume | as required |
| B) Demineralized water | 12 |
| 2,4-monofurfurylidene-1,3,5,6-O-tetra-propylsorbitol | 1 |
| Total | 100 |

A) The components A) are mixed.

B) The 2,4-monofurfurylidene-1,3,5,6-O-tetrapropylsorbitol is dissolved in the demineralized water.

The solution B) is added to the mixture A) and the new mixture is submitted to filter press.

I claim:

1. A cosmetic or dermatological composition for preventing or eliminating the effects of free radicals on the skin, said composition being in the form of a cream, gel, lotion, or spray to be used for external cutaneous application and containing as active ingredient from about 0.5 to about 2% by weight of the composition of 2,4-monofurfurylidene-sorbitol or 2,4-monofurfurylidene-1,3,5,6-O-tetralkyl-sorbitol wherein the alkyl groups are linear or branched $C_1$–$C_4$ alkyl.

2. The composition of claim 1, wherein said active ingredient is present in a quantity of from about 0.7 to about 1.5% by weight.

3. The composition of claim 1, containing as an excipient at least one member selected from the group consisting of Vaseline, a glycol, triethanolamine, and vegetable oil.

4. The composition of claim 1, further containing perfume.

5. A method for preventing or eliminating the effects of free radicals on the skin comprising topically applying to the skin an effective amount of the composition of claim 1.

* * * * *